US009457038B2

(12) United States Patent
Kaoukhov et al.

(10) Patent No.: US 9,457,038 B2
(45) Date of Patent: *Oct. 4, 2016

(54) ADMINISTRATION OF AVERMECTIN/MILBEMYCIN COMPOUNDS FOR THE TREATMENT OF OPHTHALMIC PATHOLOGIES

(71) Applicant: Galderma S.A., Cham (CH)

(72) Inventors: Alexandre Kaoukhov, Juan les Pins (FR); Christophe Villard, Le Tignet (FR); Philippe Bouissou, Rouquefort les Pins (FR)

(73) Assignee: GALDERMA S.A., Cham (CH)

( * ) Notice: Subject to any disclaimer, the term of this patent is extended or adjusted under 35 U.S.C. 154(b) by 22 days.

This patent is subject to a terminal disclaimer.

(21) Appl. No.: 14/284,524

(22) Filed: May 22, 2014

(65) Prior Publication Data

US 2014/0256662 A1 Sep. 11, 2014

Related U.S. Application Data

(63) Continuation of application No. 13/716,667, filed on Dec. 17, 2012, now Pat. No. 8,987,218, which is a continuation of application No. 13/160,408, filed on Jun. 14, 2011, now Pat. No. 8,361,974, which is a continuation of application No. 12/059,086, filed on Mar. 31, 2008, now abandoned, which is a continuation of application No. PCT/IB2006/003864, filed on Sep. 29, 2006.

(60) Provisional application No. 60/725,320, filed on Oct. 12, 2005, provisional application No. 60/818,316, filed on Jul. 5, 2006.

(30) Foreign Application Priority Data

Sep. 30, 2005 (FR) .................................. 05 10025

(51) Int. Cl.
| | |
|---|---|
| *A61K 31/7048* | (2006.01) |
| *A61K 9/06* | (2006.01) |
| *A61P 27/02* | (2006.01) |
| *A61K 9/00* | (2006.01) |

(52) U.S. Cl.
CPC ......... *A61K 31/7048* (2013.01); *A61K 9/0048* (2013.01)

(58) Field of Classification Search
CPC ................................................ A61K 31/7048
See application file for complete search history.

(56) References Cited

U.S. PATENT DOCUMENTS

| | | |
|---|---|---|
| 5,556,848 A | 9/1996 | Kimura et al. |
| 5,614,545 A | 3/1997 | Martin et al. |
| 5,952,372 A | 9/1999 | McDaniel et al. |
| 5,958,443 A | 9/1999 | Viegas et al. |
| 6,133,310 A | 10/2000 | Parks et al. |
| 7,078,048 B2 | 7/2006 | Kang et al. |
| 7,897,559 B2 | 3/2011 | Parks et al. |
| 2004/0167084 A1* | 8/2004 | Parks .............................. 514/28 |

OTHER PUBLICATIONS

Crawford, Glen H., Journal of the American Academy of Dermatology, "Rosacea: I. Etiology, pathogenesis, and subtype classification", 2004, vol. 51, No. 3, pp. 327-341.*
Wilhelmus, "Antiparasitic Drugs in Ophthamology", *International Ophthalmology Clinics*, vol. 36, No. 2, 1996, pp. 117-152, Little, Brown and Co., Boston, MA.
Bianciardi et al., "Treatment of dog thelaziosis caused by Thelazia callipaeda (Spirurida, Thelaziidae) using a topical formulation of imidacloprid 10% and moxidectin 2.5%", *Veterinary Parasitology*, 129(1-2), 2005, pp. 89-93, Elsevier B.V.
Molyneux et al., "Mass drug treatment for lymphatic filariasis and onchocerciasis," *Trends in Parasitology*, 2003 vol. 19, No. 11, pp. 516-522, Elsevier Ltd.
Cotreau et al., "The antiparasitic moxidectin: Safety, tolerability and pharmacokinetics in humans," *Journal of Clinical Pharmacology*, vol. 43, No. 9, 2003, p. 1022.
Merriam Webster's Collegiate Dictionary, tenth edition, 1996, p. 414.
*The American Heritage College Dictionary*, third edition, Houghton Mifflin Company, New York, New York, 2000, pp. xxv (Order of Senses), 294 (definition of "conjunctiva"), 310 (definition of "cornea") and 487 (definition of "eye" and "eyewash").
Official Action dated Jan. 20, 2010 in corresponding European Appln. No. 06 842 320.1, in English.
International Preliminary Report on Patentability issued for corresponding PCT/IB2006/003864, Apr. 2, 2008, in English.
International Search Report issued for corresponding PCT/IB2006/003864, Jul. 3, 2007, in English.

* cited by examiner

*Primary Examiner* — Shaojia Anna Jiang
*Assistant Examiner* — Bahar Craigo
(74) *Attorney, Agent, or Firm* — Dentons US LLP

(57) ABSTRACT

Administration of at least one compound of the family of the avermectins or of the family of the milbemycins, notably ivermectin, is useful for the treatment of ophthalmic pathologies, including ocular rosacea.

11 Claims, No Drawings

ADMINISTRATION OF AVERMECTIN/MILBEMYCIN COMPOUNDS FOR THE TREATMENT OF OPHTHALMIC PATHOLOGIES

CROSS-REFERENCE TO EARLIER APPLICATIONS

This application is a continuation of U.S. application Ser. No. 13/716,667, filed Dec. 17, 2012, now U.S. Pat. No. 8,987,218, which is a continuation of U.S. application Ser. No. 13/160,408, filed Jun. 12, 2011, now U.S. Pat. No. 8,361,974, which is a continuation of U.S. application Ser. No. 12/059,086, filed Mar. 31, 2008, abandoned, which is a continuation of PCT/IB2006/003864 filed Sep. 28, 2006 and designating the United States, published in the English language as WO 2007/054822 A2 on May 18, 2007, which claims the benefit under 35 U.S.C. §119(e) of U.S. Provisional Application No. 61/725,320, filed Oct. 12, 2005 and of U.S. Provisional Application No. 60/818,316, filed Jul. 5, 2006, and which claims foreign priority of FR 0510025, filed Sep. 30, 2005, each hereby expressly incorporated by reference in its entirety and each assigned to the assignee hereof.

BACKGROUND OF THE INVENTION

1. Technical Field of the Invention

The present invention relates to the formulation of at least one compound of the family of the avermectins or of the family of the milbemycins into pharmaceutical compositions useful for the treatment of ophthalmic pathologies, including ocular rosacea.

2. Description of Background and/or Related and/or Prior Art

Ocular rosacea is frequently diagnosed when it coexists with cutaneous signs or symptoms of rosacea (Browning D. J. and Proia A. D., Ocular Rosacea, *Surv. Ophthalmol.*, 1986, 31, 145-58). Ocular rosacea is independent of the severity of rosacea of the skin (Donshik P. C., Floss D. M. and Ehlers W. H., Inflammatory and papulosquamous disorders of the skin and eye, *Dermatologic Clinics*, 1992, 3, 533-47).

In the event of ocular attack, certain studies show more women affected than men, whereas there is no significant difference according to sex for rosacea of the skin (Ramelet A. A., Rosacea: a reaction pattern associated with ocular lesions and headache, *Arch. Dermatol.*, 1994, 130, 1448).

For a proportion of patients affected by ocular rosacea ranging up to 20%, the ocular signs and symptoms can occur before the cutaneous manifestations. The relevant symptoms for the diagnosis of ocular rosacea are as follows: feeling of burning or of smarting, feeling of a foreign body, feeling of dryness of the eye, increased sensitivity to light, blurred vision. The least serious clinical signs in patients affected by ocular rosacea are telangiectasia of the eyelid margin, meibomitis, chalazia, conjunctival hyperaemia and papillary conjunctivitis (Donshik P. C., Floss D. M. and Ehlers W. H., Inflammatory and papulosquamous disorders of the skin and eye, *Dermatologic Clinics*, 1992, 3, 533-47). Dryness of the eye with quantitative deficiency of tears and bacterial superinfection frequently exist.

More serious are the problems posed by attacks on the cornea in the form of superficial punctuate keratitis and interstitial keratitis, which can develop into a decrease in visual acuity, ulceration or perforation (Jenkins M. S., Brown S. I., Lempert S. L. and Weinberg R. J., Ocular Rosacea, *Am. J. Ophthalmol.*, 1979, 88, 618-22).

The causes of the ocular pathologies indicated above include, in particular, the presence of various organisms, such as *Demodex folliculorum*, the commonest human ectoparasite. However, not all ocular pathologies are related to the presence of this ectoparasite.

If ocular rosacea, which is included among ophthalmic pathologies, is not treated, serious complications may occur in the cornea and this can detrimentally affect the vision.

The therapeutic measures commonly employed are the application of hot compresses and of topical antibiotics, such as a metronidazole gel, for example. A marked improvement is obtained but is often followed by a relapse in the form of conjunctivitis.

Oral antibiotics, such as tetracycline hydrochloride or doxycycline, can also be administered. However, the level of relapse is on the order of 66% after treatment for 6 months (Zug K. A., Palay D. A. and Rock B., Dermatologic diagnosis and treatment of itchy red eyelids, *Surv. Ophthalmol.*, 1996, 40, 293-306). A maintenance treatment is often necessary, sometimes for several years, indeed even for life. Cyclines have an anti-inflammatory action but do not have a curative action. The longer the treatment, the more there exists a risk of appearance of resistance (Quaterman M. J., Johnson D. W., Abele D. C., Lesher J. L., Hull D. S. and Davis L. S., Ocular Rosacea, *Arch. Dermatol.*, 1997, 133, 49-54). A loss in the anti-inflammatory effectiveness is possible during long-term treatments, hence the interest in short cures (over 1 to 2 months). This treatment is used in first application, during severe attacks on the eyes, due to the risk of after-effects on the eyes.

An antibiotic of the class of the macrolides (erythromycin) can also be administered but the response to the treatment is not systematic.

Furthermore, patients suffering from ocular rosacea must not take isotretinoin, as this substance aggravates ophthalmic symptoms (Michel J. L., Valanconny C., Gain P., Montelimard N., Tchaplyguine F. and Cambazard F., Manifestations oculaires des rétinoïdes [Ocular manifestations of retinoids], *Ann. Dermatol. Venereol.*, 1998, 125, 438-42).

None of these treatments makes possible complete and lasting remission of ocular rosacea. In view of the above, there thus exists a need to formulate a composition which shows an improved effectiveness in the treatment of ocular rosacea and which does not exhibit the side effects described in the prior art.

Ivermectin is a mixture of two compounds belonging to the class of the avermectins, 5-O-demethyl-22,23-dihydroavermectin $A_{1a}$ and 5-O-demethyl-22,23-dihydroavermectin $A_{1b}$. They are also known under the names of 22,23-dihydroavermectin $B_{1a}$ and 22,23-dihydroavermectin $B_{1b}$. Ivermectin comprises at least 80% of 22,23-dihydroavermectin $B_{1a}$ and less than 20% of 22,23-dihydroavermectin $B_{1b}$. This active agent forms part of the class of the avermectins, a group of macrocyclic lactones produced by the bacterium *Streptomyces avermitilis* (Reynolds J. E. F. (Ed), (1993) Martindale, *The Extra Pharmacopoeia*, 29th Edition, Pharmaceutical Press, London).

In the mid-1980s, ivermectin was indicated as a broad-spectrum anti-parasitic medicament for veterinary application (Campbell W. C. et al. (1983), Ivermectin: a potent new anti-parasitic agent, *Science*, 221, 823-828). It is effective against the majority of common intestinal worms (except for the Teniae), the majority of the acarids and a few lice. It exhibits in particular a high affinity for the glutamate-dependent chloride channels present in the nerve and muscle cells of invertebrates. Its attachment to these channels promotes an increase in the membrane permeability to chloride ions, resulting in hyperpolarization of the nerve or muscle cell. This results in neuromuscular paralysis, which can bring about the death of certain parasites. Ivermectin also interacts with other ligand-dependent chloride channels, such as those involving the GABA (γ-aminobutyric acid) neuromediator.

Ivermectin is more particularly an anthelmintic. It is indicated in man for the treatment of onchocerciasis due to Onchocerca volvulus, of gastrointestinal strongyloidiasis (product Stromectol) and of human scabies (Meinking T. L. et al., *N. Engl. J. Med.*, 1995, Jul., 6, 331(1), 26-30, The treatment of scabies with ivermectin) and in the treatment of microfilaraemia diagnosed or suspected in subjects affected by lymphatic filariasis due to *Wuchereria bancrofti*.

Moreover, U.S. Pat. No. 6,133,310 describes the administration of invermectin topically in the treatment of rosacea of the skin, in the form of a prototype of a lotion composed of a mixture of invermectin and of water, and also indicates the possibility of a prototype of a cream composed, for its part, of the mixture of invermectin and of an excipient, such as propylene glycol or sodium lauryl sulfate, but does not describe any pharmaceutical composition as such. These mixtures are similar to experimental preparations to be applied to the skin, useful in the context of first results of a proof of concept. Specifically, the facts indicated in this patent do not suggest to one skilled in this art anything regarding the feasibility and the effectiveness of pharmaceutical compositions acceptable industrially for the treatment of ocular rosacea.

SUMMARY OF THE INVENTION

It has now surprisingly been determined that compounds of the family of the avermectins or of the family of the milbemycins, and more particularly ivermectin, are suitable for the treatment of ophthalmic pathologies of any origin, particularly ophthalmic pathologies due to *Demodex folliculorum*, and more particularly ocular rosacea.

The term "treatment" means, according to the invention, treatment in man.

The present invention thus features formulation of at least one compound selected from among the family of the avermectins and the family of the milbemycins into unique pharmaceutical compositions useful for the treatment of ophthalmic pathologies, particularly ophthalmic pathologies due to *Demodex folliculorum*, and more particularly ocular rosacea, whether regime or regimen.

The term "pharmaceutical composition" means, according to the invention, a stable composition comprising a therapeutically active agent which has a good cosmetic quality and a satisfactory time limit (18 months minimum).

According to the invention, the term "unique pharmaceutical composition" means that the composition comprising the compound(s) of the family of avermectins and/or of the family of the milbemycins is administered alone to treat the ophthalmic pathologies; combinations with other pharmaceutical compositions are thus excluded.

Preferably, according to the present invention, the compound(s) of the family of the avermectins and/or of the family of the milbemycins is (are) the only active principle(s) employed in the composition for treating ophthalmic pathologies; no active principle other than the avermectins and milbemycins, whether in particular administered topically or orally, is employed according to the invention.

The term "avermectins" means in particular a compound selected from among ivermectin, invermectin, avermectin, abamectin, doramectin, eprinomectin, emamectin and selamectin.

The term "milbemycins" means in particular a compound selected from among lepimectin, milbemectin, milbemycin oxime and moxidectin, nemadectin.

The compound selected is preferably ivermectin.

The present invention also features formulation of ivermectin into pharmaceutical compositions useful for the treatment of ophthalmic pathologies, particularly ophthalmic pathologies due to *Demodex folliculorum*, and more particularly ocular rosacea.

DETAILED DESCRIPTION OF BEST MODE AND SPECIFIC/PREFERRED EMBODIMENTS OF THE INVENTION

The pharmaceutical compositions according to the invention, comprising at least one compound selected from among the family of the avermectins and the family of the milbemycins, and preferably ivermectin, are particularly useful for the treatment of ophthalmic symptoms, symptoms selected from a feeling or sensation of burning or of smarting of the eye, a feeling or sensation of a foreign body in the eye, a feeling or sensation of dryness of the eye, an increased sensitivity to light, blurred vision, telangiectasia of the eyelid margin, meibomitis, chalazia, conjunctival hyperaemia and papillary conjunctivitis.

According to another embodiment of the invention, the pharmaceutical composition comprising at least one compound selected from the family of the avermectins and the family of the milbemycins, and preferably ivermectin, is administered in particular for the treatment of conjunctivitis or blepharitis.

The pharmaceutical compositions according to the invention are useful for the treatment of the eyes topically, orally, parenterally or rectally.

The topical application is the most common method of administration of ophthalmic medicaments. The topical route makes possible the instillation into the eye of drops or the application in the eye of solutions, eyewashes, suspensions, salves, ointments, gels, sprays, foams, powders, lotions, viscoelastic solutions and/or the deploying of solid forms at the surface of the eye, impregnated pads, syndets or wipes.

Same can also be provided in the form of suspensions of microspheres or nanospheres or of vesicles formed from lipid or polymer or of polymeric patches and of hydrogels making possible controlled release. These compositions for topical application can be provided in anhydrous form, in aqueous form or in the form of an emulsion.

The pharmaceutical compositions for topical application must be non-irritating and compatible with the tissues of the eye. The solutions are sterile preparations free from all particles. The suspensions are sterile preparations comprising solid particles in a liquid vehicle appropriate for ocular instillation. The ointments are semisolid and sterile preparations.

Orally, the pharmaceutical compositions can be provided in liquid, pasty or solid form, in the form of powders and more particularly in the form of tablets, including sugar-coated tablets, hard gelatin capsules, syrups, suspensions, solutions, powders, granules, emulsions, microspheres or nanospheres or vesicles formed from lipid or polymer making possible controlled release.

Parenterally, the compositions can be provided in the form of solutions or suspensions for infusion or for injection.

Rectally, the compositions can be provided in the form of suppositories.

The compositions according to the invention preferably comprise from 0.001% to 10% of at least one compound selected from the family of the avermectins and the family of the milbemycins, preferably ivermectin, by weight with respect to the total weight of the composition. More preferably, the compositions according to the invention comprise from 0.01% to 5% of at least one compound selected from the family of the avermectins and the family of the milbemycins, preferably ivermectin, by weight with respect to the total weight of the composition.

In a preferred alternative embodiment of the invention, the subject pharmaceutical compositions are for topical application.

More preferably, the compositions according to the invention are provided in the form of an eyewash or of eye drops. The term "eyewash" means a liquid formulation specifically appropriate for administration to the conjunctiva of the eye and the cornea. The eyewash is characterized by a volume of the instilled drops of approximately 25-50 microliters.

As indicated above, the compositions according to the invention have to meet specific conditions in order to be applied in the eye. Such conditions include, in particular, sterility, absence of irritation and compatibility with the tissues of the eye. The latter criterion is more difficult to obtain than for a composition applied to the skin; in particular, compounds such as ethanol or glycols, formulated in compositions to be applied to the skin, cannot be included in compositions for ocular use.

The topical compositions according to the invention make it possible to directly and specifically treat the symptoms of the pathology in the eye and eyelids by a local action; in particular, since only the eye is targeted, a better effectiveness can be expected.

Furthermore, the topical compositions according to the invention preferably being the only ones administered to treat ocular rosacea, interactions from active principles can be reduced, indeed even avoided.

The pharmaceutical compositions according to the invention can additionally comprise inert additives or combinations of these additives, such as:
wetting agents, emollients;
agents for improving flavor;
preservatives;
stabilizing agents;
agents for regulating moisture;
pH-regulating agents;
buffers;
agents for modifying osmotic pressure;
emulsifying agents;
agents for increasing viscosity;
and antioxidants.

Of course, one skilled in this art will take care to choose the optional compound or compounds to be added to these compositions such that the advantageous properties intrinsically associated with the present invention are not, or not substantially, detrimentally affected by the envisaged addition.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

| | |
|---|---|
| Ivermectin | 0.03% |
| Polysorbate 80 | 2.00% |
| Benzalkonium chloride | 0.05% |
| EDTA | 0.05% |
| Water | q.s. for 100 |
| Buffer system pH 6.3 | |

Example 2

| | |
|---|---|
| Ivermectin | 0.10% |
| Polysorbate 80 | 5.00% |
| Phenylethyl alcohol | 0.50% |
| Hydroxypropylcellulose | 1.20% |
| Sorbitol | 2.00% |
| Water | q.s. for 100 |
| Monosodium phosphate/sodium sulfite heptahydrate (buffer system) | q.s. pH 6.5 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed:

1. A method of treating ocular rosacea in the eye(s), wherein the method comprises topically administering directly to the conjunctiva and/or to the cornea(s) of the eye(s) of an individual in need of such treatment, a topical composition comprising an effective amount of ivermectin and a pharmaceutically acceptable vehicle, wherein ivermectin is the sole active ingredient for treating ocular rosacea in the topical composition.

2. The method as defined by claim 1, wherein the composition is in the form of an ointment.

3. The method as defined by claim 2, wherein the composition comprises 0.001% to 10% by weight of ivermectin relative to the total weight of the composition.

4. The method as defined by claim 3, wherein the composition comprises 0.001% to 0.10% by weight of ivermectin relative to the total weight of the composition.

5. The method as defined by claim 3, wherein the composition comprises 0.01% to 0.5% by weight of ivermectin relative to the total weight of the composition.

6. The method as defined by claim 3, wherein the composition comprises 0.01% to 0.10% by weight of ivermectin relative to the total weight of the composition.

7. The method as defined by claim 3, wherein the composition comprises 0.03% by weight of ivermectin relative to the total weight of the composition.

8. The method as defined by claim 3, wherein the composition comprises 0.10% by weight of ivermectin relative to the total weight of the composition.

9. A method of treating symptoms of ocular rosacea in the eye(s), wherein the method comprises topically administering directly to the conjunctiva and/or to the cornea(s) of the eye(s) of an individual in need of such treatment, a topical composition comprising an effective amount of ivermectin, and a pharmaceutically acceptable vehicle, wherein ivermectin is the sole active ingredient for treating ocular rosacea in the topical composition.

10. The method as defined by claim 9, wherein the topical composition is in the form of an ointment.

11. The method as defined by claim 10, wherein the symptoms are selected from the group consisting of a feeling of burning of the eye, a feeling of smarting of the eye, a feeling of dryness of the eye, an increased sensitivity to light, blurred vision, and a complication of ocular rosacea in the cornea.

\* \* \* \* \*